(12) United States Patent
Ali

(10) Patent No.: US 6,497,237 B1
(45) Date of Patent: Dec. 24, 2002

(54) DENTAL FLOSSING SYSTEM

(76) Inventor: Sayel A. Ali, 1501 - 37th Ave. South, Fargo, ND (US) 58104

( * ) Notice: Subject to any disclaimer, the term of this patent is extended or adjusted under 35 U.S.C. 154(b) by 0 days.

(21) Appl. No.: 09/877,889

(22) Filed: Jun. 7, 2001

(51) Int. Cl.$^7$ ............................................. A61C 15/00
(52) U.S. Cl. .................. 132/324; 132/323; 132/326; 132/329
(58) Field of Search ........................ 132/324, 323, 132/325, 326, 327, 328, 329

(56) References Cited

U.S. PATENT DOCUMENTS

| | | | | |
|---|---|---|---|---|
| 1,287,926 A | * | 12/1918 | Ecaubert | 132/324 |
| 4,586,521 A | * | 5/1986 | Urso | 132/324 |
| 4,660,584 A | * | 4/1987 | Wofford | 132/324 |
| 4,936,326 A | * | 6/1990 | Eckroat | 132/326 |
| 4,995,361 A | * | 2/1991 | Lorenzana et al. | 132/324 |

* cited by examiner

Primary Examiner—John J. Wilson
Assistant Examiner—Robyn Kieu Doan

(57) ABSTRACT

A dental flossing system for allowing an individual to floss their teeth with only one hand and without positioning their fingers within their mouth during flossing. The dental flossing system includes a body having a pair of arms and a rear portion containing a spool rotatably positioned within, a platform structure movably positioned within the body, a wheel is rotatably attached within the platform structure, a shaft concentrically attached to the wheel and extending from a side of the platform structure for receiving a length of dental floss, and a locking arm that is pivotally attached to the platform structure for locking the dental floss in a desired position within a locking groove.

20 Claims, 4 Drawing Sheets

DENTAL FLOSSING SYSTEM

BACKGROUND OF THE INVENTION

1. Field of the Invention

The present invention relates generally to dental flossing devices and more specifically it relates to a dental flossing system for allowing an individual to floss their teeth with only one hand and without positioning their fingers within their mouth during flossing.

2. Description of the Prior Art

The use of dental floss is considered to be of great importance in the exercise of healthy dental hygiene. Dentists recommend at least daily use of dental floss in conjunction with brushing to promote health, teeth and gums. Because of the difficulty and discomfort of flossing the teeth, many flossing devices have been developed in the prior art.

A first class of such prior art devices includes non-motorized flossing stationary flossing devices. For example, the dental cleansing device shown in U.S. Pat. No. 5,094,256 to Barth ("Barth") includes a fork-shaped device having two arms extending from the distal end of a shaft. One end of a length of dental floss is fastened to the shaft. From the shaft, the floss is strung through an aperture in one arm, through an aperture in a second art, and strung down to and fastened to the shaft at the other end. The floss is strung tightly between the two fastening points to provide a tight length of floss between the arms of the device. The user then holds the operative end of the shaft and positions tight length of shaft between abutting teeth. The user causes cleansing action to take place by moving the shaft in a reciprocating manner, which movement is directly translated to the floss.

The drawback of this and similar devices are that only the small length of floss between the arms is available for cleansing at any one time, and gets dirty and worn quickly, requiring constant restringing. Further more, the reciprocating motion of the arms within the mouth can cause the arms to hit and irritate the gums and cheeks.

Another group of fork-shaped devices include a motorized mechanism for causing movement of the dental floss relative to the shaft and thus the teeth. In U.S. Pat. No. 5,184,632 to Gross et al. ("Gross et al."), a length of floss is secured such that it extends tautly between two arms of the device. A motor causes circular motion of the floss to effectuate cleaning action. Another device shown in U.S. Pat. No. 5,224,500 to Stella ("Stella") shows a motor and cam mechanism that causes a length of floss to reciprocate between two arms. The reciprocating floss movement effectuates cleaning when the floss is inserted around or between abutting teeth.

Motorized flossing devices such as the Stella device provide floss movement without requiring the movement of the shaft or arms of the structure. As a result, they provide an advantage over devices such as that described in Barth in that floss motion is achieved without having to effectuate motion of the arms within the mouth. A drawback of the motorized flossing devices is that they are mechanically complex, presenting manufacturing difficulty and reliability questions. A further drawback of such devices is that they require a source of power, such as batteries. Finally, such devices involve the placement of an electrical appliance into the mouth, thereby requiring extra safety mechanisms to be employed.

Another problem inherent with flossing devices is the requirement of steady arm control during use. In the use of flossing devices, only small controlled movements, or in some cases no movement at all, is required. Such control over the flossing device can cause the user to experience hand and arm fatigue. Consequently, a need exists for a flossing device that when used, requires less control and thereby reduces hand and arm fatigue.

Another patent related to the present invention is U.S. Pat. No. 5,799,674 to Ali et al. entitled "Dental Flossing Device." Ali et al. overcomes many of the problems with conventional dental floss devices. However, Ali et al. does not provide a convenient mechanism for dispensing, locking and removing the dental floss during usage. The present invention provides a structure that overcomes the limitations of Ali et al.

While these devices may be suitable for the particular purpose to which they address, they are not as suitable for allowing an individual to floss their teeth with only one hand and without positioning their fingers within their mouth during flossing. Conventional dental floss devices are difficult to utilize and require both hands to properly operate.

In these respects, the dental flossing system according to the present invention substantially departs from the conventional concepts and designs of the prior art, and in so doing provides an apparatus primarily developed for the purpose of allowing an individual to floss their teeth with only one hand and without positioning their fingers within their mouth during flossing.

SUMMARY OF THE INVENTION

In view of the foregoing disadvantages inherent in the known types of dental flossing devices now present in the prior art, the present invention provides a new dental flossing system construction wherein the same can be utilized for allowing an individual to floss their teeth with only one hand and without positioning their fingers within their mouth during flossing.

The general purpose of the present invention, which will be described subsequently in greater detail, is to provide a new dental flossing system that has many of the advantages of the dental flossing devices mentioned heretofore and many novel features that result in a new dental flossing system which is not anticipated, rendered obvious, suggested, or even implied by any of the prior art dental flossing devices, either alone or in any combination thereof.

To attain this, the present invention generally comprises a body having a pair of arms and a rear portion containing a spool rotatably positioned within, a wheel is rotatably attached within a central portion of the body, a shaft concentrically attached to the wheel and extending from a side of the body for receiving a length of dental floss, and a locking arm that is pivotally attached to the body for locking the dental floss in a desired position within a locking groove.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a dental flossing system that will overcome the shortcomings of the prior art devices.

A second object is to provide a dental flossing system for allowing an individual to floss their teeth with only one hand and without positioning their fingers within their mouth during flossing.

Another object is to provide a dental flossing system that allows for a continuous and clean length of dental floss to be utilized without requiring cutting or reloading each time an individual flosses their teeth.

An additional object is to provide a dental flossing system that is convenient to utilize.

A further object is to provide a dental flossing system that is comprised of a simple construction.

Another object is to provide a dental flossing system that may be utilized by users of all ages and abilities.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
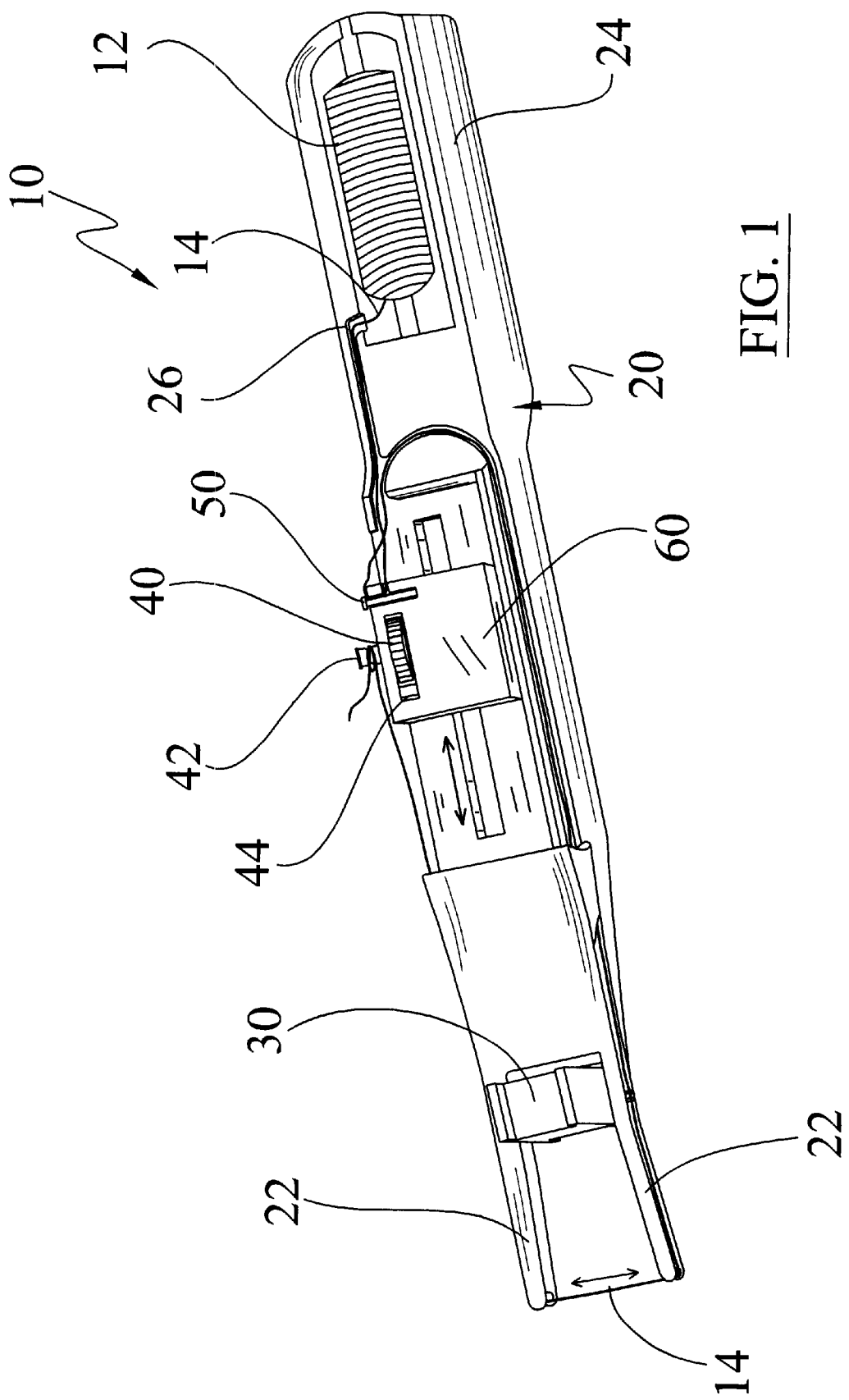
FIG. 1 is an upper perspective view of the present invention.
Figure 2:
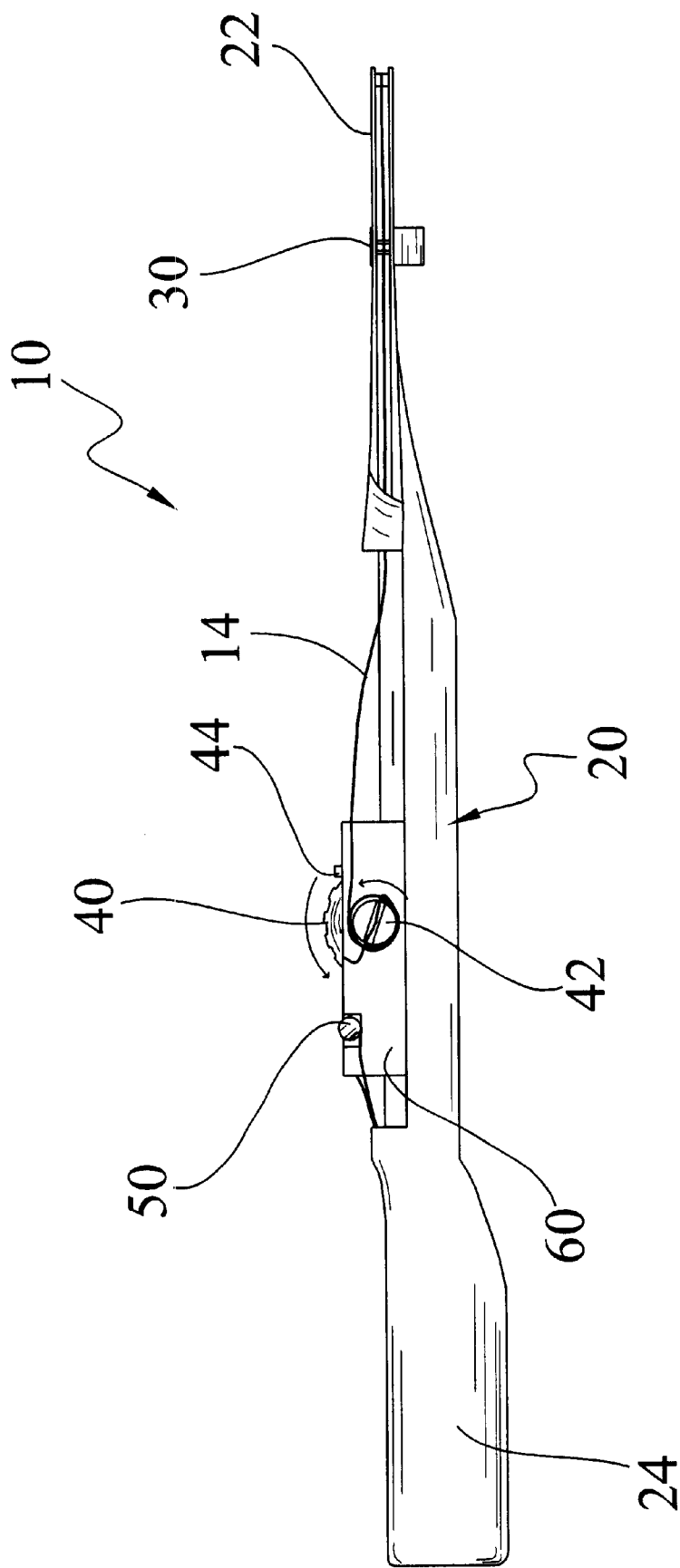
FIG. 2 is a side view of the present invention illustrating the rotational movement of the wheel and shaft.

Turning now descriptively to the drawings, in which similar reference characters denote similar elements throughout the several views, FIGS. 1 through 4 illustrate a dental flossing system 10, which comprises a body 20 having a pair of arms 22 and a rear portion 24 containing a spool 12 ratably positioned within, a platform structure 60 movably positioned within the body 20, a wheel 40 is rotatable attached within the platform structure 60, a shaft 42 concentrically attached to the wheel 40 and extending from a side of the body 20 for receiving a length of dental floss 14, and a locking arm 50 that is pivotally attached to the platform structure 60 for locking the dental floss 14 in a desired position within a locking groove 52.

As shown in FIG. 1 through 4 of the drawings, the body 20 is comprised of an elongate structure. The body 20 preferably includes a pair of arms 22 extending a finite distance from an end of the body 20 for receiving a length of dental floss 14 and allowing for the insertion of the tensioned dental floss 14 between the teeth of the user. The body 20 includes a rear portion 24 that rotatably receives a spool 12 containing a length of dental floss 14. The body 20 may or may not include a leverage member 30 for assisting in manipulating the dental floss 14 between the teeth. The spool 12 may have various shapes and the dental floss 14 may be comprised of any conventional flossing string.

The following patent is considered relevant to the body 20 structure, the spool 12, the arms 22 and the dental floss of the present invention and is incorporated herein by reference: U.S. Pat. No. 5,799,674. The aforementioned patent, of which is mentioned elsewhere in this disclosure, and which forms a part of this disclosure, may be applied in known manner by those skilled in the art in order to practice various embodiments of the present invention.

A channel 26 within the body 20 receives the dental floss 14 as the dental floss 14 leave the spool 12 rotatably attached within. The channel 26 extend substantially parallel to a longitudinal axis of the body 20 as best shown in FIGS. 1 and 4 of the drawings. The channel 26 is of sufficient width and depth to allow the dental floss 14 within to move freely without significant interference. The end of the channel 26 opposite of the spool 12 exits the side of the body 20 at an angle traverse to the longitudinal axis of the body 20 as best shown in FIGS. 3 and 4 of the drawings.

Figure 3:
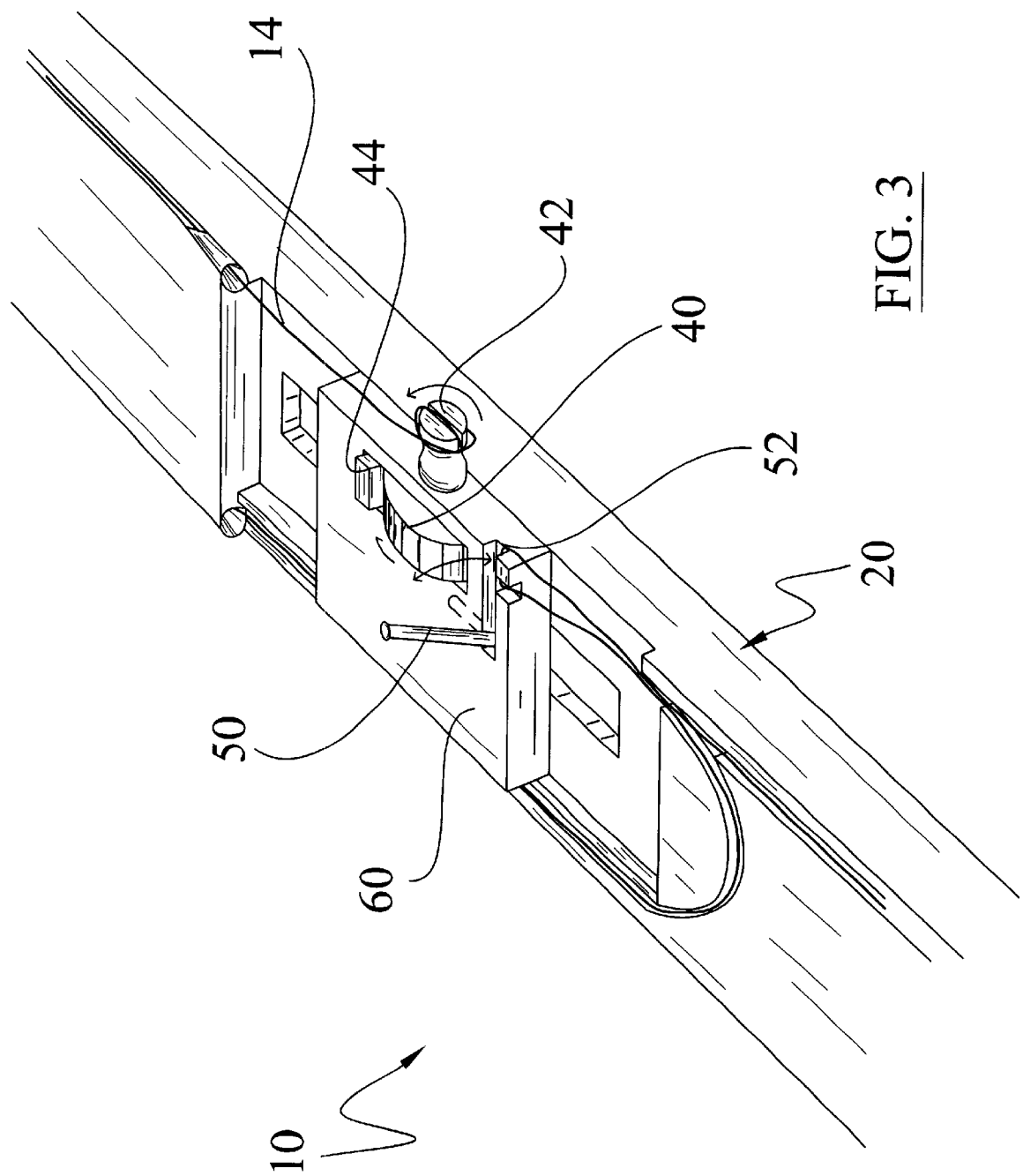
FIG. 3 is a magnified upper perspective view of the present invention illustrating the rotational movement of the wheel and shaft.
Figure 4:
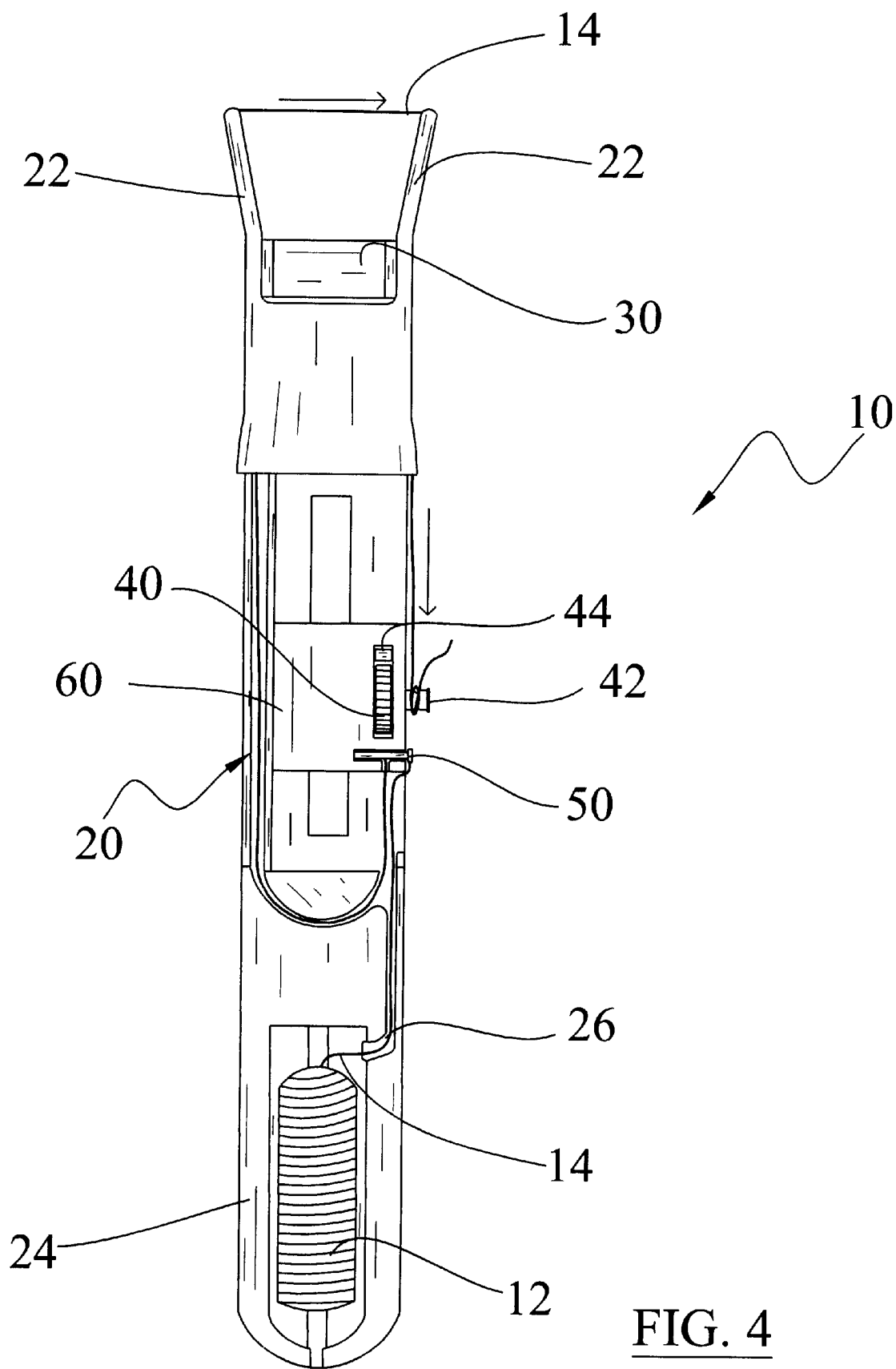
FIG. 4 is a top view of the present invention illustrating the movement of the dental floss during operation of the present invention.

A locking groove 52 is positioned within the platform structure 60 or body 20 that extends substantially parallel to the end portion of the channel 26 as best illustrated in FIG. 3 of the drawings. The locking groove 52 is formed for receiving the locking arm 50 that is pivotally attached to the platform structure 60 or body 20 as further shown in FIG. 3 of the drawings. The channel 26 continues form the locking groove 52 extending to one of the arms 22 as best shown in FIG. 4 of the drawings. The length of dental floss 14 continues through the locking groove 52 back into the channel 26 extending through the arms 22 as shown in FIG. 4 of the drawings. The locking arm 50 is pivoted into the locking groove 52 thereby frictionally engaging the dental floss 14 for preventing movement thereof after the dental floss 14 is in the desired position.

As shown in FIGS. 1 through 4 of the drawings, the platform structure 60 is movably positioned upon the body 20. The platform structure 60 may have various shapes as can be appreciated. The platform structure 60 preferably moves along a longitudinal axis upon the body 20 within a slot or other longitudinal structure as clearly defined within U.S. Pat. No. 5,799,674 which is hereby incorporated by reference.

As shown in FIGS. 1 through 4 of the drawings, a wheel 40 is rotatably positioned within a slot within the platform structure 60. It can be appreciated that the wheel 40 may also be attached directly within the body 20 instead of the platform structure 60. The wheel 40 preferably includes a plurality of gripping ridges to facilitate gripping thereof by a user. A stopper 44 is positioned within the body 20 that is selectively manipulated to engage the wheel 40 thereby selectively preventing or allowing rotation of the wheel 40. It can be appreciated that the stopper 44 may be comprised of an automatic catch mechanism that allows wheel 40 to rotate in only the tightening direction thereby not requiring additional manipulation by the user and preventing reverse rotation of the wheel 40 during usage.

A shaft 42 extends concentrically from the wheel 40 exterior of the platform structure 60 or the body 20 as best illustrated in FIGS. 3 and 4 of the drawings. The distal portion of the shaft 42 includes a radial groove for receiving a length of the dental floss 14 form the arms 22 as best shown in FIG. 3 of the drawings. The end of the shaft 42 includes a slot that extends longitudinally through the end portion of the shaft 42 for receiving an initial portion of the dental floss 14.

In use, the user first must pass the distal end of the dental floss 14 form the spool 12 through the channel 26 within the body 20 to the middle exit portion of the channel 26 adjacent the locking groove 52. The user then extends the dental floss 14 about the corner through the locking groove 52 then back through the channel 26 thereafter extending through the pair of arms 22 as shown in FIG. 4 of the drawings. The user then manipulates the dental floss 14 by extending the same through the slot within the distal end of the shaft 42 and manually wraps a length of the dental floss 14 about the shaft 42 to maintain the dental floss 14 about the shaft 42 by effectively "tying" the dental floss 14 about the shaft 42. The user then manipulates the locking arm 50 within the locking groove 52 thereby preventing movement of the dental floss 14 opposite of the shaft 42. The user then manipulates the wheel 40 to tighten the dental floss 14 into a taut state and thereafter manipulates the stopper 44 to prevent movement of the wheel 40. It can be appreciated that the stopper 44 may be comprised of an automatic catch mechanism that allows the wheel 40 to rotate in only the tightening direction thereby not requiring additional manipulation by the user. The user then slides the platform structure 60 back and forth causing the floss 14 to move between the arms 22 while the user provides up and down movements between the teeth. When the user requires a clean and unused portion of the dental floss 14 between the arms 22, the user simply releases the locking arm 50 and rotates the wheel 40 to draw the dental floss 14 from the spool 12 through the channel 26. The user then locks the locking arm 50 within the locking groove 52 to prevent movement of dental floss 14 and thereafter may further tighten the dental floss 14 by providing additional rotation of the wheel 40. In addition, when the shaft 42 has accumulate a significant amount of dental floss 14 over time, the user simply severs the dental floss 14 adjacent to the shaft 42 and unwinds the accumulated dental floss 14 form the shaft 42. The user then repeats the above process to reinstate the dental floss 14.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A dental flossing system, comprising:
   a body having a pair of arms for receiving a length of dental floss between thereof;
   a channel having a first portion and a second portion within said body;
   a spool containing said dental floss rotatably positioned within said body, wherein said dental floss extends from said spool through said channel;
   a locking groove positioned between said first portion and said second portion of said channel; and
   a locking arm pivotally attached to said body within said locking groove for allowing selective engagement of a portion of said dental floss within said locking groove.

2. The dental flossing system of claim 1, including a wheel rotatably positioned within said body, and a shaft concentrically extending from said wheel through said body for receiving a distal portion of said dental floss.

3. The dental flossing system of claim 2, including a means for preventing reverse rotation of said wheel.

4. The dental flossing system of claim 3, wherein said shaft includes a radial groove.

5. The dental flossing system of claim 4, wherein said shaft includes a slot extending into a distal end thereof opposite of said wheel.

6. The dental flossing system of claim 5, wherein an end portion of said first portion of said channel is substantially traverse to a longitudinal axis of said body.

7. The dental flossing system of claim 6, wherein said locking groove is substantially parallel to said end portion of said first portion of said channel.

8. The dental flossing system of claim 7, wherein said second portion of said channel extends into said locking groove.

9. The dental flossing system of claim 8, wherein said means for preventing reverse rotation of said wheel is comprised of a stopper.

10. The dental flossing system of claim 9, wherein said wheel has a radial plane parallel to a longitudinal axis of said body.

11. A dental flossing system, comprising:
    a body having a structure for receiving a length of dental floss between thereof;
    a channel having a first portion and a second portion within said body;
    a spool containing said dental floss rotatably positioned within said body, wherein said dental floss extends from said spool through said channel;
    a locking groove positioned between said first portion and said second portion of said channel; and
    a locking arm pivotally attached to said body within said locking groove for allowing selective engagement of a portion of said dental floss within said locking groove.

12. The dental flossing system of claim 11, including a platform structure slidably attached to said body and a wheel rotatably positioned within said platform structure, and a shaft concentrically extending from said wheel through said platform structure for receiving a distal portion of said dental floss.

13. The dental flossing system of claim 12, including a means for preventing reverse rotation of said wheel.

14. The dental flossing system of claim 13, wherein said shaft includes a radial groove.

15. The dental flossing system of claim 14, wherein said shaft includes a slot extending into a distal end thereof opposite of said wheel.

16. The dental flossing system of claim 15, wherein an end portion of said first portion of said channel is substantially traverse to a longitudinal axis of said body.

17. The dental flossing system of claim 16, wherein said locking groove is substantially parallel to said end portion of said first portion of said channel.

18. The dental flossing system of claim 17, wherein said second portion of said channel extends into said locking groove.

19. The dental flossing system of claim 18, wherein said means for preventing reverse rotation of said wheel is comprised of a stopper.

20. The dental flossing system of claim 19, wherein said wheel has a radial plane parallel to a longitudinal axis of said body.

* * * * *